United States Patent
Solomons et al.

(10) Patent No.: US 10,286,036 B2
(45) Date of Patent: May 14, 2019

(54) PROTOCOL FOR TREATMENT OF LUPUS NEPHRITIS

(71) Applicant: AURINIA PHARMACEUTICALS INC., Victoria (CA)

(72) Inventors: Neil Solomons, Victoria (CA); Robert B. Huizinga, North Saanich (CA)

(73) Assignee: AURINIA PHARMACEUTICALS INC., Victoria (CA)

( * ) Notice: Subject to any disclaimer, the term of this patent is extended or adjusted under 35 U.S.C. 154(b) by 0 days.

(21) Appl. No.: 15/835,219

(22) Filed: Dec. 7, 2017

(65) Prior Publication Data

US 2018/0325995 A1    Nov. 15, 2018

Related U.S. Application Data

(60) Provisional application No. 62/541,612, filed on Aug. 4, 2017, provisional application No. 62/505,734, filed on May 12, 2017.

(51) Int. Cl.
| | |
|---|---|
| *A61K 38/13* | (2006.01) |
| *A61K 31/365* | (2006.01) |
| *A61K 31/573* | (2006.01) |

(52) U.S. Cl.
CPC ............ *A61K 38/13* (2013.01); *A61K 31/365* (2013.01); *A61K 31/573* (2013.01)

(58) Field of Classification Search
CPC .... A61K 31/365; A61K 31/436; A61K 38/13; A61K 38/00
See application file for complete search history.

(56) References Cited

U.S. PATENT DOCUMENTS

| | | | |
|---|---|---|---|
| 5,712,084 A | 1/1998 | Osgood | |
| 6,998,385 B2 | 2/2006 | Naicker et al. | |
| 7,060,672 B2 | 6/2006 | Naicker et al. | |
| 7,332,472 B2 | 2/2008 | Naicker et al. | |
| 7,429,562 B2 | 9/2008 | Naicker et al. | |
| 7,482,327 B2 | 1/2009 | Hagerty et al. | |
| 7,829,533 B2 | 11/2010 | Naicker et al. | |
| 9,679,115 B2 | 6/2017 | Frey | |
| 2004/0167197 A1 | 8/2004 | Rudolph et al. | |

OTHER PUBLICATIONS

Aurinia Pharmaceuticals, Clinical trials.gov, AURA-LV: Aurinia Urinary Protein Reduction Active—Lupus With Voclosporin (AURA-LV) (AURA-LV), NCT02141672 , published online 2014.*
Hanns-Martin Lorenz, Treatment of active lupus nephritis with the novel immunosuppressant 15-deoxyspergualin: an open-label dose escalation study, Lorenz et al. Arthritis Research & Therapy 2011, 13:R36.*
Astellas Pharma US, Inc., "PROGRAF® (tacrolimus) capsules, USP; PROGRAF® (tacrolimus) injection," Rx prescribing information (2015).
AURA, "Aurion Study Data Review," Presentation. Dated Sep. 27, 2016.
Aurinia Pharmaceuticals, "Aurinia Announces Voclosporin Meets 48-Week Remission Endpoints, Achieving Highest Complete Remission Rate of Any Global Lupus Nephritis Study," Dated Mar. 1, 2017, 4 pages.
Aurinia Pharmaceuticals, "Aurion Data presentation," (2016) 6 pages.
Aurinia Pharmaceuticals, "Aurion study: 48-week data of multi-target therapy with Voclosporin, MMF and steroids for active lupus nephritis," Presentation. (2016).
Aurinia Pharmaceuticals, "Safety in recent global lupus nephritis trials, voclosporin and AURA," Presentation (2016) 16 pages.
Bao et al., "Successful treatment of class V+IV lupus nephritis with myltitarget therapy," J Am Soc Nephrol (2008) 19:2001-2010.
Chen et al., "Short-term Outcomes of Induction Therapy With Tacrolimus Versus Cyclophosphamide for Active Lupus Nephritis: A Multicenter Randomized Clinical Trial," Am J Kidney Dis (2011) 57(2):235-244.
Corapi et al., "Comparison and evaluation of lupus nephritis response criteria in lupus activity indices and clinical trials," Arthritis Research & Therapy (2015) 17:110.
Cortes-Hernandez et al., "Long-term outcomes—mycophenolate mofetil treatment for lupus nephritis with addition of tacrolimus for resistant cases," Nephrol Dial Transplant (2010) 25:3948-3956.
Dooley et al., "Speed of Remission with the use of Voclosporin, MMF and low dose steroids: results of a global lupus nephritis study," Abstract. Retrieved on https://acr.confex.com/acr/2016/late/papers/index.cgi?username=61565&password=329286. Retrieved on Oct. 3, 2016.
Dooley et al., "Speed of Remission with the Use of Voclosporin, MMF and Low Dose Steroids: Results of a Global Lupus Nephritis Study," Presentation. (2016) 30 pages.
Fu et al., "Clinical efficacy of cyclosporin a neoral in the treatment of paediatric lupus nephritis with heavy proteinuria," British Journal of Rheumatology (1998) 37:217-221.
Hannah et al., "Tacrolimus use in lupus nephritis: A systematic review and meta-analysis," Autoimmunity Reviews (2016) 15:93-101.
Huizinga et al., "AURION study: 24-week data of multi-target therapy with voclosporin, MMF and steroids for active lupus nephritis," Abstract. 10th European Lupus Meeting, Venice, Oct. 5-8, 2016.
Ishii et al., "Influence of renal complications on the efficacy and adverse events of tacrolimus combination therapy in patients with systemic lupus erythematosus (SLE) during a maintenance phase: a single-centre, prospective study," Lupus Science & Medicine (2015) 2:e000091.

(Continued)

*Primary Examiner* — James H Alstrum-Acevedo
*Assistant Examiner* — Erinne R Dabkowski
(74) *Attorney, Agent, or Firm* — Morrison & Foerster LLP

(57) ABSTRACT

By employing a pharmacodynamic dosing regimen, the effectiveness of a protocol for treatment of lupus nephritis with voclosporin can be maximized while minimizing undesirable side effects.

13 Claims, 1 Drawing Sheet

(56) References Cited

OTHER PUBLICATIONS

Jones, "Estimating Renal Function for Drug Dosing Decisions," Clin Biochem Rev (2011) 32:81-88.

Kraaij et al., "TAC-TIC use of tacrolimus-based regimens in lupus nephritis," Lupus Science & Medicine (2016) 3:e000169.

Lee et al., "Relative efficacy and safety of tacrolimus, mycophenolate mofetil, and cyclophosphamide as induction therapy for lupus nephritis: a Bayesian network meta-analysis of randomized controlled trials," Lupus (2015) 24:1520-1528.

Ling et al., "Cytochrome P450 3A and P-glycoprotein drug-drug interactions with voclosporin," Br J Clin Pharmacol (2013) 77(6):1039-1050.

Liu et al., "Multitarget Therapy for Induction Treatment of Lupus Nephritis A Randomized, Controlled Trial," Ann Intern Med (2015) 162(1):18-26.

Mayo et al., "Voclosporin Food Effect and Single Oral Ascending Dose Pharmacokinetic and Pharmacodynamic Studies in Healthy Human Subject," The Journal of Clinical Pharmacology (2013) 53(8):819-826.

Miwa et al., "Steroid-Sparing Effect of Tacrolimus in the Maintenance Phase of Systemic Lupus Erythematosus: A Single-Center, Prospective Study," Clinical and Experimental Medical Sciences (2014) 2(3):75-86.

Miyasaka et al., "Efficacy and safety of tacrolimus for lupus nephritis: a placebo-controlled double-blind multicenter study," Mod Rheumatol (2009) 19:606-615.

Mok et al., "Effect of Renal Disease on the Standardized Mortality Ratio and Life Expectancy of Patients With Systemic Lupus Erythematosus," Arthritis & Rheumatism (2013) 65(8):2154-2160.

Mok et al., "Tacrolimus versus mycophenolate mofetil for induction therapy of lupus nephritis: a randomized controlled trial and long-term follow-up," Ann Rheum Dis (2016) 75:30-36.

NOVARTIS Pharmaceuticals Corporation, "NEORAL® Soft Gelatin Capsules (cyclosporine capsules, USP) Modified; NEORAL® Oral Solution (cyclosporine oral solution, USP) Modified," Rx prescribing information (2009).

Pendergraft et al., "AURALV: Successful treatment of active lupus nephritis with voclosporin," Draft Preview of Abstract #6480. Retrieved on http://www.call4abstracts.com/asn16_system/c4a/preview.php Retrieved on Sep. 6, 2016.

Pendergraft et al., "AURALV: Successful treatment of active lupus nephritis with voclosporin," Presentation. Dated Nov. 19, 2016. 25 pages.

Solomons et al., "MP130 Aurion study: Multi-target therapy with Voclosporin, MMF and steroids for lupus nephritis," Nephrol Dial Transplant (2016) 31(suppl_1):i385.

Szeto et al., "Tacrolimus for the treatment of systemic lupus erythematosus with pure class V nephritis," Rheumatology (2008) 47:1678-1681.

Uchino et al., "Safety and potential efficacy of tacrolimus for treatment of lupus nephritis with persistent proteinuria," Clinical and Experimental Rheumatology (2010) 28:6-12.

Yahya et al., "Aurion Study: 12 Week Data of Multi-Target Therapy with Voclosporin, MMF and steroids for lupus nephritis," Presentation. (2016) 19 pages.

Yahya et al., "AURION study: 24-week data of multi-target therapy with voclosporin, MMF and steroids for active lupus nephritis," Aurion Lupus Final Abstract. Dated Oct. 31, 2016.

Yang et al., "Calcineurin inhibitors may be a reasonable alternative to cyclophosphamide in the induction treatment of active lupus nephritis: A systematic review and meta-analysis," Experimental and Therapeutic Medicine (2014) 7:1663-1670.

Zhang et al., "The effect of calcineurin inhibitors in the induction and maintenance treatment of lupus nephritis: a systematic review and meta-analysis," Int Urol Nephrol (2016) 48(5):731-743.

Aurinia Pharmaceuticals, "Aurinia Pharmaceuticals Announces Voclosporin Meets Primary Endpoint in Phase IIB AURA-LV Study in Lupus Nephritis," Published Aug. 15, 2016. Retrieved from https://ir.auriniapharma.com/press-releases/detail/49/aurinia-pharmaceuticals-announces-voclosporin-meets-primary. Retrieved on Dec. 12, 2018.

Aurinia Pharmaceuticals, "Aurinia Announces Voclosporin Meets 48-Week Remission Endpoints, Achieving Highest Complete Remission Rate of Any Global Lupus Nephritis Study," Published Mar. 1, 2017. Retrieved from https://ir.auriniapharma.com/press-releases/detail/73/aurinia-announces-voclosporin-meets-48-week-remission. Retrieved on Dec. 12, 2018.

Huizinga et al., "AURION Study: 48-week data of multi-target therapy with voclosporin, MMF and steroids for active lupus nephritis," Presented Mar. 26-29, 2017. Retrieved from http://c.eqcdn.com/_349da054eda96a4b6781a0902e2929ab/auriniaphanna/db/246/9I0/pdf/LUPUS+2017?+Presentation FINAL.pdf>. Retrieved on Dec. 12, 2018.

Aurinia Pharmaceuticals, "Aurinia highlights 48-week data from open-label AURION study," Published Mar. 27, 2017. Retrieved from https://ir.auriniaphanna.com/press-releases/detail/81. Retrieved on Dec. 12, 2018.

Aurinia Pharmaceuticals, "Aurinia releases additional 48-week data from the AURA-LV Study during late-breaking session," National Kidney Foundation. Dated Apr. 20, 2017. Retrieved from https://ir.auriniapharma.com/press-releases/detail/85/aurinia-releases-additional-48-week-data-from-the-aura-lv. Retrieved on Dec. 13, 2018.

* cited by examiner

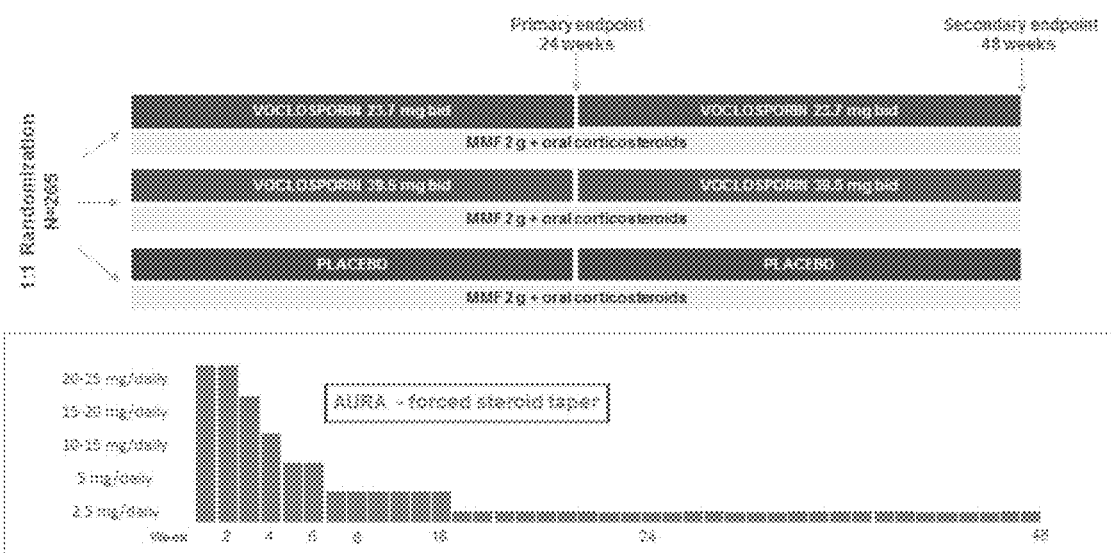

PROTOCOL FOR TREATMENT OF LUPUS NEPHRITIS

CROSS-REFERENCE TO RELATED APPLICATIONS

This application claims benefit under 35 U.S.C. Section 119(e) of U.S. Provisional Patent Application Nos. 62/505,734, filed 12 May 2017, and 62/541,612, filed 4 Aug. 2017. The contents of the above patent applications are incorporated by reference herein in their entirety.

TECHNICAL FIELD

The invention relates to treatment of lupus nephritis with voclosporin. More specifically it relates to pharmacodynamic dosing of subjects in accordance with an improved protocol for treatment.

BACKGROUND ART

Lupus nephritis (LN) one of a number of proteinuric kidney diseases wherein an inflammation of the kidneys is caused by systemic lupus erythematosus (SLE) whereby up to 60% of SLE patients develop LN. LN is a debilitating and costly disease often leading to renal failure which requires dialysis, or renal transplant and often results in death. Indeed, patients with renal failure have an over 60-fold increased risk of premature death compared to SLE patients in general. A clinical sign of LN is leakage of blood proteins into the urine and the disease can be diagnosed by a number of factors, including urinary protein/creatinine ratio (UPCR) wherein a UPCR of greater than 0.5 mg/mg is indicative of the condition being in an active state. Further, certain markers in the blood can also be diagnostic—for example, complement 3 (C3), complement 4 (C4) and anti-dsDNA antibodies.

The standard of care for LN has not met with a great deal of success. The standard of care is use of mycophenolate mofetil (MMF) or intravenous cyclophosphamide. With these treatments partial remission was found only in approximately 50% of cases and complete remission was shown in less than 10% of the subjects. Thus, there is clearly a need for a treatment that improves these outcomes.

Voclosporin is an analog of cyclosporin A that has been found useful for treating autoimmune diseases and as an immunosuppressant in organ transplantation.

Mixtures of the E and Z isomers of voclosporin are described in U.S. Pat. No. 6,998,385. Mixtures with a preponderance of the E-isomer are described in U.S. Pat. No. 7,332,472. The '472 patent describes a number of indications which can be treated with the isomeric voclosporin mixture including glomerulonephritis. However, although some animal studies are described, no protocols in humans are disclosed.

Various formulations of voclosporin mixtures are also described in U.S. Pat. Nos. 7,060,672; 7,429,562 and 7,829,533.

In October 2016, the results of a clinical study conducted on behalf of Aurinia Pharmaceuticals were published as an abstract. According to the abstract, the subjects, who were afflicted with lupus nephritis (LN), were dosed with 23.7 mg of voclosporin twice daily in combination with mycophenolate mofetil (MMF) and reducing cortical steroid dose over 24 weeks for which data were presented. Entry criteria for the study included determination of a urine protein creatinine ratio (UPCR) of ≥1.0 mg/mg or ≥1.5 mg/mg depending on the classification of a renal biopsy and an eGFR (estimated glomerular filtration rate) of ≥45 mol/mn/1.73 m$^2$ as well as serologic evidence of LN. The results of this protocol showed complete remission or partial remission in a large percentage of subjects.

In addition, it was shown that subjects who achieved a ≥25% reduction in UPCR at 8 weeks were likely to maintain benefit throughout the 24-week protocol.

In a news release sent by Aurinia Pharmaceuticals on 1 Mar. 2017, the results of more extensive clinical study involving mycophenolate mofetil (MMF) and reducing corticosterone dosages, but using in addition to 23.7 mg of voclosporin twice daily, a higher dose of 39.5 mg twice daily were described. The results of this study showed successful complete or partial remission in a large number of patients at 24 weeks and 48 weeks. It appeared that the lower dosage of 23.7 mg twice daily (BID) was even more effective than the higher dosage of 39.5 mg twice daily (BID).

It has now been found that successful results, including a diminution in the number and severity of side effects can be obtained by altering the protocols disclosed in these publications by providing a pharmacodynamic dosing schedule based on individual patient responses. In addition, it has been found that even lower dosages of voclosporin—i.e., 15.8 mg of voclosporin twice daily or 7.9 mg of voclosporin twice daily are effective.

DISCLOSURE OF THE INVENTION

The present invention, thus, provides an improved protocol for treatment of lupus nephritis or other proteinuric kidney diseases that takes advantage of assessments of parameters associated with the response of individual subjects. The invention is a personalized form of a protocol for treatment of LN including protocols that employ low dosage of voclosporin. The voclosporin used is preferably a mixture of greater than about 80% E isomer and less than about 20% Z isomer, and more preferably greater than about 90% E isomer and less than about 10% Z isomer. The protocol employs daily dosages of voclosporin over a projected period of 24, 48, 52 weeks or longer wherein the voclosporin is administered twice daily (BID). Suitable dosages are in increments of 7.9 mg including 39.5 mg, 31.6 mg, 23.7 mg, 15.8 mg or 7.9 mg. Low dosages may show superior results compared to a higher dose of 39.5 mg each of such administrations carried out twice daily. The protocol preferably further includes administering to the subject an effective amount of MMF and/or an effective amount of a corticosteroid, typically prednisone, in a reducing dosage level across the time period of the study.

While it has been verified that the protocols of the invention are effective for lupus nephritis, such results indicate the same protocols can be used to generally treat proteinuric kidney diseases. Proteinuric kidney diseases that can be treated include: Diabetic nephropathy, nephrotic syndromes (i.e. intrinsic renal failure), nephritic syndromes, toxic lesions of kidneys, glomerular diseases, such as membranous glomerulonephritis, focal segmental glomerulosclerosis (FSGS), IgA nephropathy (i.e., Berger's disease), IgM nephropathy, membranoproliferative glomerulonephritis, membranous nephropathy, minimal change disease, hypertensive nephrosclerosis and interstitial nephritis.

One of the side effects of treatment with voclosporin is an unwanted decrease in the estimated glomerular filtration rate (eGFR). The present protocol is designed to reduce the incidents of this undesirable side effect by adjusting the dosage in accordance with the response of the subject.

Thus, in one aspect, the invention is directed to a pharmacodynamic method to treat a proteinuric kidney disease which method comprises administering to a subject diagnosed with said disease a predetermined daily dosage of effective amounts of voclosporin over a projected treatment period of at least 24 weeks, said pharmacodynamic method further comprising:

(a) assessing the estimated Glomerular Filtration Rate (eGFR) of said subject at at least a first time point and a second time point on different days of said treatment period, and (b) (i) if the eGFR of said subject decreases by more than a target % to below a predetermined value between said first and second time points, reducing the daily dosage by increment(s) of 7.9 mg BID or stopping the administering of voclosporin to said subject;

(ii) if the eGFR of said subject decreases by less than said target % between said first and second time points, continuing administering the same predetermined daily dosage of voclosporin to said subject.

In one specific embodiment, the invention includes a pharmacodynamic method to treat lupus nephritis which method comprises administering to a subject diagnosed with lupus nephritis a predetermined daily dosage of effective amounts of voclosporin over a projected treatment period of at least 24 weeks, said pharmacodynamic method further comprising:

(a) assessing the glomerular filtration rate (eGFR) of said subject at at least a first time point and a second time point on different days of said treatment period, and (b) (i) if the eGFR of said subject decreases by ≥30% to a value of below 60 mL/min/1.73 m$^2$ between said first and second time points, stopping the administering of voclosporin to said subject;

(ii) if the eGFR of said subject decreases by between 20% to 30% to a value of below 60 ml/min/1.73 m$^2$ between said first and second time points, administering a reduced dosage of voclosporin to said subject;

(iii) if the eGFR of said subject decreases by ≤20% between said first and second time points, continuing administering the same predetermined daily dosage of voclosporin to said subject.

The eGFR of 60 mL/min/1.73 m$^2$ noted above is typically used; however, higher values such as 90 mL/min/1.73 m$^2$ or 75 or 70 mL/min/1.73 m$^2$ or lower value such as 50 mL/min/1.73 m$^2$ or 55 mL/min/1.73 m$^2$ could also be used.

In general, the pharmacodynamic method may employ a third time point subsequent to the first and second time point wherein the target percentage reduction is again determined and if the percentage reduction as compared to the first time point is less than the target percentage treatment may be restored, or if the percentage decrease is greater than the target percentage exhibited at the second time point, further reduction in dosage may be indicated.

It has also been found that the effectiveness of the protocol can be evaluated after only a portion of the treatment period has elapsed. Therefore, because it is generally undesirable to continue an ineffective treatment, an assessment at approximately one third of the period of the protocol or between 7-9 weeks after the beginning of the protocol is conducted and if the effectiveness of treatment is not confirmed, the treatment is terminated.

For example, the assessment may include determining the UPCR at first and second time points early in the protocol wherein the first point is determined at the outset of the protocol and stopping the administration of voclosporin to the subject if the UPCR has not been reduced by ≥25% at the second time point. The UPCR can be determined by any standard technique, e.g., using first morning void or a 24 hour urine sample.

In any of the protocols above, preferably, a dosage of MMF and a reducing dosage of corticosteroid is also administered during the treatment period. Typically, MMF is administered at the level of 2 grams daily and oral corticosteroids are administered in daily dosages diminishing from 20-25 mg daily to 2.5 mg daily over a period of 16 weeks. The reduced dosages then continue throughout the study. These protocols are shown in FIG. 1.

In all cases, subjects who would be amenable to this treatment are identified by screening said subject prior to conducting said method on said subject by:

(a) determining that the urine protein creatinine ratio (UPCR) of said subject is ≥1.5 mg/mg or ≥1 mg/mg depending on renal biopsy as preferably measured by first morning void; and (b) determining said subject has an eGFR as measured by the Chronic Kidney Disease Epidemiology Collaboration equation (CKD-EPI) of ≥45 mL/min/1.73 m$^2$ or any other suitable method such as the Modification of Diet in Renal Disease (MDRD) Study equation. If the determinations of subparagraphs (a) and (b) are positive, the subject is considered suitable for subjection to the protocol.

In addition, lowered levels of corticosteroid dosage have been shown to be effective.

It is also advantageous and part of the invention to evaluate a subject who has been treated with the protocol at the end of the treatment period to determine whether a complete or partial remission has occurred. Further evaluations are included at a time subsequent to termination of the treatment to assess whether the remission achieved according to the measurement at the end of the treatment is being maintained. Such evaluation may also be done at intermediate times during treatment to determine whether dosage can be reduced. In an exemplary embodiment used simply for illustration a dosage of 23.6 mg voclosporin BID may be reduced to 15.8 mg or 7.9 mg BID based on such results.

The evaluation for effectiveness can be based on the protein/creatinine ratio in urine (UPCR) where a ratio of ≤0.5 mg/mg indicates complete response; alternatively, or in addition, an eGFR of ≥60 mL/min/1.73 m$^2$ or no decrease from baseline and eGFR of ≥20% is shown. Other indications of complete response include lack of need for rescue medications such as intravenous steroids, cyclophosphamide or a need for ≤10 mg prednisone for more than three consecutive days or more than seven days total. These evaluations may be performed at any point in the treatment.

BRIEF DESCRIPTION OF THE DRAWINGS

FIG. 1 shows graphically the design of a protocol for treatment of lupus nephritis with voclosporin upon which the pharmacodynamic treatment of the invention is superimposed.

MODES OF CARRYING OUT THE INVENTION

As noted above, the pharmacodynamic protocol of the invention relates to adjustment of administration of voclosporin depending on certain physiological indicators of the subjects. As further noted, the voclosporin administration is preferably conducted with a background of administration of MMF and of corticosteroids.

For example, with respect to corticosteroids, subjects who weigh 45 kg or more may receive 0.5 grams of methylprednisolone on days 1 and 2 of the study intravenously and then beginning on day 3, oral corticosteroid therapy. Subjects weighing ≤45 kg receive only half these dosages.

For oral prednisone, the starting dosage for oral administration is 20 mg/day for subjects <45 kg and 25 mg/day for subjects who weigh ≥45 kg. The dosage is reduced according to the protocol shown in Table 1.

TABLE 1

Dosing Schedule for IV Methylprednisolone and Daily Oral Prednisone (mg)

|  | Subjects <45 kg | Subjects ≥45 kg | In Case of Prior IV Steroids During Screening (Pre-randomization) |
|---|---|---|---|
| Weeks 1-2[1] |  |  |  |
| Days 1-2[2] | 0.25 g (IV) | 0.5 g (IV) | 1 g minus prior IV steroids mg or (0.5 g minus prior IV steroids mg for subjects who weigh <45 kg)[3] |
| Days 3-13 | 20 mg (oral) | 25 mg (oral) |  |
| Week 2 (Day 14) | 15 mg (oral) | 20 mg (oral) |  |
| Week 4 (Day 28) | 10 mg (oral) | 15 mg (oral) |  |
| Week 6 (Day 42)[4] | 10 mg (oral) | 10 mg (oral) |  |
| Week 8 (Day 56) | 5 mg (oral) | 5 mg (oral) |  |
| Week 12 (Day 84) | 5 mg (oral) | 5 mg (oral) |  |
| Week 16 (Day 112) | 2.5 mg (oral) | 2.5 mg (oral) |  |

[1]Day 0-13: Oral steroids dosed according to subject weight and then tapered beginning at Day 14.
[2]Oral corticosteroids may be commenced on Days 1 or 2 if corticosteroids are administered during screening.
[3]It is recognized that dosing with IV methylprednisolone as described in Section 7.2.2.2, Corticosteroids may not be in the subject's best interest if they have already received therapy within the 3 months prior to screening. In this case, the investigator may be permitted to omit the administration of further IV methylprednisolone but only after discussion with the Medical Monitor.
[4]Week 6 is not a scheduled study visit, a phone call can be performed to decide further tapering for subjects.
Notes:
Oral prednisone taper should be done within ±3 days of specified timeframe. When clinically indicated, subjects are allowed to be completely titrated off of oral corticosteroids.
Abbreviation:
IV = Intravenous.

In contrast to the reducing dose of corticosteroid, the same dose of MMF is maintained throughout the study at a twice daily dosage before meals with a glass of water. Typically, each individual dose is one gram resulting in a total dosage of two grams per day although in the alternative, the subject may be administered 500 mg four times daily.

Critical to the present invention is pharmacodynamic administration of the voclosporin component. This is essential as the effects of this drug may be too intense or the results may indicate lack of effectiveness and thus the dosage is reduced or interrupted to permit homeostasis to reestablish a suitable set of physiological parameters.

As noted above, the protocols are designed to cover treatment periods of at least 24 weeks and may extend for longer periods of time. The regimens involve daily dosages of the voclosporin component, typically twice daily, although alternative frequencies could be employed, such as once a day, three times a day or four times a day based on reactions of the patient and convenience. As an illustration, the protocol will be described below in terms of a 23.7 mg twice daily (BID) dosage; of course if the voclosporin preparation is administered four times daily, the dosage would be cut in half for each administration and if the administration were only once per day, the dosage for the once a day administration would be double the 23.7 mg administered BID.

In addition, as to the pharmacodynamic protocols of the invention, the dosages may be any combination of the 7.9 mg basic units, and thus can be 7.9 mg, 15.8 mg, 31.6 mg, or 39.5 mg, as well as the exemplified 23.7 mg.

The dosage indicated, for example 23.7 mg, is subject to slight variations, typically ±10% or, alternatively, between 21 mg and 26 mg BID. This is due to inconsistencies in pharmaceutical manufacture and the ideal dosage is 23.7 mg BID. Comparable variations applied to the alternative dosages.

One critical parameter used to assess the desirability of dosage reduction is the eGFR using the CKD-EP1 formula or other appropriate method. Chronic kidney disease is defined as eGFR as ≤60 mL/min/1.73 m$^2$ for ≥three months with or without kidney damage. As noted above, a decrease in eGFR is a negative side effect that may occur during treatment. If the decrease is too severe, the protocol should be altered in accordance with the prescription of the invention. Typically, a baseline value of the eGFR is established either at the beginning of the protocol or at some "first time point" during the protocol. If the decrease is greater than a target percentage, which is typically between 20%-45% as compared to the first time point, a reduction in dosage is indicated, including a reduction to zero or stopping treatment. If the decrease is less than that target percentage maintenance of treatment at the same level as indicated. In addition to an indication that treatment should be reduced or terminated based on the eGFR reduction, reduction below a certain value is also indicative of a need to modify the treatment. This predetermined value is typically in the range of 50-90 mL/min/1.73 m$^2$.

As stated above, a baseline value for eGFR is established at the outset of the treatment or during treatment. This is typically done on the first day of the treatment before any administration of the drugs in the protocol. This baseline is used as a criterion for adjusting dosage. However, a first time point could be established at any arbitrarily selected time during the protocol.

In one exemplary protocol, at a second time point subsequent to the first which can be on any day of the treatment, a subject with ≥30% decrease in eGFR from the baseline to <60 ml/min/1.73 m$^2$ (or, in some cases, a higher cut off) should have the treatment interrupted until a repeat test can be performed, but if the decrease is confirmed and not due to contributing factors (such as a high baseline eGFR, the addition or modification of non-steroidal anti-inflammatory drugs, angiotensin converting enzyme inhibitors, angiotensin 2 inhibitor blockers, or a concurrent state of dehydration, etc.), the treatment should be withheld until a third time point determination typically within 48 hours. If the ≥30% decrease is not maintained, treatment is restored to two-thirds or one-third of the original dosage and increased as tolerated to the 23.7 mg level BID.

For convenience, the 23.7 mg administration is administered orally in the form of three capsules containing 7.9 mg each. Thus, it is easy to provide two-thirds of the standard dosage by administering at any given time only two of the three capsules.

With regard to the second time point, in this exemplary protocol a subject having a decrease of ≥20% in eGFR to ≤60 mL/min/1.73 m² but a decrease of less than 30% reduction as compared to baseline, the treatment is not interrupted but the dosage is reduced. Reduction in increments of 7.9 mg is preferred. Again, assessment at an additional time point at any subsequent day during the treatment showing baseline values are restored indicates that the original dosage level of 23.7 mg BID can be resumed.

It has also been found that a determination early in a 24-week protocol of probable success can be used to determine whether treatment with voclosporin should continue. For example, if the UPCR has not been reduced by ≥25% early in the regimen, the chances of improvement over an extended treatment period are diminished. Typically, such determination can be made at approximately 8 weeks subsequent to the beginning of the regimen; a time frame of 6-10 weeks could be employed for the approximation of 8 weeks. If a decrease of ≥25% of UPCR is not achieved, it appears unlikely the subject will benefit from further treatment and the protocol is stopped.

In all cases, the subjects are evaluated for success of the treatment both on the completion of the treatment and at extended periods thereafter. Typical treatment periods are at least 24 weeks, but preferably 48 weeks or more. Reevaluation after the termination of the treatment period over a period of 1-2 weeks or longer is also employed. Subjects are evaluated for complete or partial remission. Complete remission (CR) is defined as: Confirmed protein/creatinine ratio of ≤0.5 mg/mg, and eGFR≥60 mL/min/1.73 m² or no confirmed decrease from baseline in eGFR of ≥20%. Partial remission is defined as: 50% reduction in UPCR from baseline.

By establishing a pharmacodynamic dosing regimen, the effectiveness of the protocol in treatment of lupus nephritis can be maximized while minimizing undesirable side effects.

The length of the treatment protocol in all cases will vary from at least 8 weeks to for example 12, 16, 24 and 48 weeks or 52 weeks or even longer, up to 60 weeks including stopping points between the levels mentioned. For example, a treatment protocol of 10 or 11 or 15 or 20 or 29 or 31 or 36 or 43 or 51 or 55 weeks could be employed and is within the scope of the invention. The evaluation described above is conducted at the end of the protocol as well as at a suitable time period or multiple time periods thereafter. These time periods are generally 1-2 weeks to 4-5 months subsequent to terminating the dosage and intervening at time intervals are included within the scope of the invention as well.

This statement regarding time intervals applies to the invention pharmacodynamic treatment protocols, regardless of base dosage levels.

The following examples are to illustrate, not to limit the invention.

Example 1

48 Week Study of LN Treatment

The subjects enrolled in the study were divided into three groups, 88 subjects are in a control group who were administered 2 g MMF daily as well as oral corticosteroids—i.e., prednisone in a tapering dosage shown graphically in FIG. 1—beginning at 20-25 mg daily reduced gradually after the 12$^{th}$ week to 2.5 mg daily. 89 subjects in the low dosage group received this background treatment, but in addition were administered three capsules containing 7.9 mg (i.e. 23.7 mg) of voclosporin each twice daily. The voclosporin used in this study comprised greater than 90% E isomer. A third group which was comprised of 88 subjects received a similar background treatment but in addition were dosed with five 7.9 mg capsules i.e. 39.5 mg twice daily. The study was conducted over a period of 48 weeks and safety was evaluated at 24 weeks.

Subjects were screened prior to admission to the study by (a) determining that the urine protein creatinine ratio (UPCR) as >1.5 mg/mg as measured by first morning void, and (b) that the eGFR as measured by Chronic Kidney Disease Epidemiology Collaboration equation (CKD-EP1) of >45 ml/min/1.73 m². Subjects were assessed after 24 weeks and 48 weeks as well as a subsequent evaluation at 50 weeks.

The low dosage administration achieved better results than administration of voclosporin at higher dosages. Briefly, 32.6% of low dosage patients showed CR at 24 weeks compared to 19.3% of controls and 70% showed PR compared to 49% of controls.

CR in this example is a composite end-point which includes efficacy, safety and low-dose steroids: UPCR≤0.5 mg/mg (confirmed); eGFR>60 ml/min/1.73 m2 or within 20% of baseline; steroids ≤10 mg/day; no administration of rescue medication.

PR is a composite end-point that includes safety and efficacy: UPCR reduction of 50% from baseline and no use of rescue medication To determine the efficacy of the pharmacodynamic protocol wherein dosage is reduced or stopped according to the presence or absence of indicators of the decrease in eGFR experienced as a side effect, these three groups of patients were assessed after 24 weeks and 48 weeks of treatment inconsideration of whether treatment was altered according to the invention protocol. In all three groups, the patients were evaluated according to the criteria set forth in the exemplary protocol above—i.e., wherein the eGFR of each patient was measured immediately prior to administering the first dose of voclosporin and at a second time point at least a day later and (i) if the eGFR of said subject decreases by ≥30% to a value of below 60 mL/min/1.73 m² between said first and second time points, stopping the administering of voclosporin to said subject;

(ii) if the eGFR of said subject decreases by between 20% to 30% to a value of below 60 ml/min/1.73 m² between said first and second time points, administering a reduced dosage of voclosporin to said subject;

(iii) if the eGFR of said subject decreases by ≤20% between said first and second time points, continuing administering the same predetermined daily dosage of voclosporin to said subject.

The results are shown in Tables 2 and 3 below. Table 2 shows percentages with complete remission (CR) or partial remission (PR) after 24 weeks and Table 3 shows these values after 48 weeks for patients that had no dose reduction and those who did have dose reduction.

TABLE 2

Patients with a No Dose Reductions (24 weeks):

| Group | Patient number (n) | Patients with no Dose Reduction n (%) | Patients with CR at 24 weeks n (%) | Patients with PR at 24 weeks n (%) |
|---|---|---|---|---|
| Placebo | 88 | 77 (87.5) | 14 (18.2) | 36 (46.8) |
| Low Dose | 89 | 50 (56.2) | 15 (30.0) | 34 (68.0) |
| High Dose | 88 | 41 (46.6) | 11 (26.8) | 24 (58.5) |

Patients with Dose Reductions (pharmacodynamically dosed):

| Group | Patient number (n) | Patients with Dose Reduction n (%) | Patients with CR at 24 weeks n (%) | Patients with PR at 24 weeks n (%) |
|---|---|---|---|---|
| Placebo | 88 | 11 (12.5) | 3 (27.3) | 7 (63.6) |
| Low Dose | 89 | 39 (43.8) | 14 (35.9) | 28 (71.8) |
| High Dose | 88 | 47 (53.4) | 13 (27.7) | 34 (72.3) |

TABLE 3

Patients with No Dose Reductions (48 weeks):

| Group | Patient number (n) | Patients with no Dose Reduction n (%) | Patients with CR at 48 weeks n (%) | Patients with PR at 48 weeks n (%) |
|---|---|---|---|---|
| Placebo | 88 | 74 (84.1) | 18 (24.3) | 38 (51.4) |
| Low Dose | 89 | 43 (48.3) | 20 (46.5) | 26 (60.5) |
| High Dose | 88 | 35 (39.8) | 11 (31.4) | 22 (62.9) |

Patients with Dose Reductions (pharmacodynamically dosed):

| Group | Patient number (n) | Patients with Dose Reduction n (%) | Patients with CR at 48 weeks n (%) | Patients with PR at 48 weeks n (%) |
|---|---|---|---|---|
| Placebo | 88 | 14 (15.9) | 3 (21.4) | 4 (28.6) |
| Low Dose | 89 | 46 (51.7) | 24 (52.2) | 35 (76.1) |
| High Dose | 88 | 53 (60.2) | 24 (45.3) | 41 (77.4) |

In this study, CR was defined as a composite of UPCR≤0.5 mg/mg; eGFR>60 mL/min/1.73 m² or within 20% of baseline, steroids at ≤10 mg/day and no administration of rescue medication. PR is defined as UPCR reduction of 50% from baseline and no use of rescue medication.

As shown in Table 4, after 24 weeks, 12.5% of patients on placebo, 43.8% of patients on low dose and 53.4% of patients on high dose voclosporin underwent dose reduction during the treatment. The percentage of patients with complete response was not affected in either dosage groups by the pharmacodynamic dosage and the percentage with partial response was also roughly the same, although with the high dose group, the percentage with partial reduction improved. Table 5 shows similar results at 48 weeks, although a higher percentage of patients were subjected to dose reduction. Again, no drastic effect on the overall response was exhibited.

Example 2

Low Dosage Protocol

In the course of clinical studies similar to those in Example 1, it was observed that a substantial portion of subjects showed substantial remission at a dosage reduced almost immediately to 15.8 mg voclosporin administered twice daily (BID). Accordingly, applicants have analyzed these data and have concluded that a dosage protocol providing 15.8 mg or 7.9 mg voclosporin BID is effective with or without the pharmacodynamic aspects of the protocol.

As the capsules contain 7.9 mg voclosporin, 1 cap represents 7.9 mg voclosporin, 2 caps represent 15.8 mg voclosporin and 3 caps represent 23.7 mg voclosporin, etc. Substantial numbers of subjects showed complete or partial remission even when the dosage was lowered to 7.9 mg voclosporin BID quite early in the treatment and similar results were obtained for administration of 15.8 mg BID.

Example 3

Low Dose Corticosteroid

Applicants have also found that the dosage of corticosteroid can effectively be reduced as compared to "standard of care" as shown in Tables 2 and 3, and can be reduced further to 4 mg per day or less.

TABLE 4

Standard of Care Dosing Schedule for IV methylprednisolone and daily oral prednisone:

| Time | Patients <45 kg (daily dosage) | Patients ≥45 kg (daily dosage) |
|---|---|---|
| Days 1-3 | 0.5 g IV methylprednisolone | 1 g IV methylprednisolone |
| Days 3-112 | 1 mg/kg tapered down | 1 mg/kg (maximum 80 mg) tapered down |

TABLE 5

Lowered Dosing Schedule for IV methylprednisolone and daily oral prednisone:

| Time | Patients <45 kg (daily dosage) | Patients ≥45 kg (daily dosage) |
|---|---|---|
| Days 1-2 | 0.25 g IV methylprednisolone | 0.5 g IV methylprednisolone |
| Days 3-13 | 20 mg oral prednisone | 25 mg oral prednisone |
| Week 3 | 15 mg oral prednisone | 20 mg oral prednisone |
| Week 4 | 10 mg oral prednisone | 15 mg oral prednisone |
| Week 6 | 10 mg oral prednisone | 10 mg oral prednisone |
| Week 8 | 5 mg oral prednisone | 5 mg oral prednisone |
| Week 12 | 5 mg oral prednisone | 5 mg oral prednisone |
| Week 16 | 2.5 mg oral prednisone | 2.5 mg oral prednisone |

The invention claimed is:

1. A pharmacodynamic method to treat a proteinuric kidney disease which method comprises administering to a subject diagnosed with said disease a predetermined daily dosage of an effective amounts of voclosporin over a projected treatment period of at least 24 weeks, said pharmacodynamic method further comprising:
(a) assessing the estimated Glomerular Filtration Rate (eGFR) of said subject at at least a first time point and a second time point on different days of said treatment period, and
(b) (i) if the eGFR of said subject decreases by more than a target % in the range of 20-45% to below a predetermined value in the range of 50-90 ml/min/1.73 m² between said first and second time points, reducing the daily dosage by increment(s) of 7.9 mg BID or stopping the administering of voclosporin to said subject;
(ii) if the eGFR of said subject decreases by less than said target % between said first and second time points, continuing administering the same predetermined daily dosage of voclosporin to said subject.

2. The method of claim 1 wherein the first time point is immediately preceding administering voclosporin.

3. The method of claim 1 wherein the predetermined value is approximately 60 ml/min/1.73 m$^2$.

4. The method of claim 1 wherein the target % is approximately 30%.

5. The method of claim 1 which further includes identifying said subject as appropriate for said method prior to conducting said method on said subject by:
(a) determining that the urine protein creatinine ratio (UPCR) of said subject is >1 mg/mg as measured by first morning void or 24 hour urine; and
(b) determining said subject has an eGFR as measured by Chronic Kidney Disease Epidemiology Collaboration equation (CKD-EP1) of >45 ml/min/1.73 m$^2$,
wherein if (a) and (b) are met, said subject is identified as appropriate for said method.

6. The method of claim 1 wherein said predetermined daily dosage is 39.5. mg voclosporin BID, 31.6 mg voclosporin BID, 23.7 mg voclosporin BID, 15.8 mg voclosporin BID or 7.9 mg voclosporin BID.

7. The method of claim 1 wherein said method further includes evaluating said subject for renal function at a time point after the end of said treatment period by assessing eGFR.

8. The method of claim 7 wherein said method further includes evaluating said subject for maintaining renal function by assessing protein/creatinine ratio (UPCR) at a time point after the end of said treatment period.

9. The method of claim 1 wherein said method further includes administering to said subject an effective amount of mycophenolate mofetil (MMF).

10. The method of claim 1 which further includes administering to said subject an effective amount of a corticosteroid.

11. The method of claim 1 wherein said treatment period is at least 48 weeks.

12. The method of claim 1 which further includes determining the eGFR of said subject at a third time point and if the eGFR is determined at said third time point to differ from the eGFR determined at said first time point by less than said target %, resuming administering said predetermined daily dosage of voclosporin.

13. The method of claim 12 wherein the target % is approximately 30%.

* * * * *